(12) United States Patent
Wherry, III et al.

(10) Patent No.: US 6,451,289 B2
(45) Date of Patent: Sep. 17, 2002

(54) ALBUTEROL FORMULATIONS

(75) Inventors: Robert J. Wherry, III, Nashua, NH (US); Stewart H. Mueller, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/815,150

(22) Filed: Mar. 22, 2001

Related U.S. Application Data

(60) Provisional application No. 60/191,910, filed on Mar. 24, 2000.

(51) Int. Cl.$^7$ .......................... A61K 9/12; A61K 31/135
(52) U.S. Cl. .......................... 424/45; 424/401; 514/653; 560/42; 206/204
(58) Field of Search ...................... 424/45, 401; 560/42; 206/204; 514/653

(56) References Cited

U.S. PATENT DOCUMENTS

| | | | |
|---|---|---|---|
| 4,206,758 A | 6/1980 | Hallworth et al. | 128/203 |
| 4,353,365 A | 10/1982 | Hallworth et al. | 128/203 |
| 4,499,108 A | 2/1985 | Sequeira et al. | 514/653 |
| 4,751,071 A | 6/1988 | Magruder et al. | 424/467 |
| 4,777,049 A | 10/1988 | Magruder et al. | 424/457 |
| 4,851,229 A | 7/1989 | Magruder et al. | 424/457 |
| 5,362,755 A | 11/1994 | Barberich et al. | 514/649 |
| 5,545,745 A * | 8/1996 | Gao et al. | 560/42 |
| 6,113,927 A * | 9/2000 | Hatakeyama | 424/401 |
| 6,119,853 A * | 9/2000 | Garrill et al. | 206/204 |

OTHER PUBLICATIONS

Schering, Drug Information on Proventil®, revised Aug. 1999 (obtained through on-line PDR).*

* cited by examiner

Primary Examiner—Jose' G. Dees
Assistant Examiner—M. Haghighatian
(74) Attorney, Agent, or Firm—Heslin Rothenberg Farley & Mesiti P.C.; Mary Louise Gioeni

(57) ABSTRACT

Albuterol formulations packaged in an oxygen-permeable plastic container have a long shelf life at room temperature. The formulations consist essentially of albuterol or a pharmaceutically acceptable salt thereof, sodium chloride, and water, have a pH of about 4, and contain less than 0.08% by weight of albuterol aldehyde and less than 1 ppm dissolved oxygen.

20 Claims, 3 Drawing Sheets

ALBUTEROL FORMULATIONS

CROSS-REFERENCE TO RELATED APPLICATIONS

This application claims the benefit of U.S. Provisional Application No. 60/191,910, filed Mar. 24, 2000.

FIELD OF THE INVENTION

The invention relates to packaged albuterol formulations having a long shelf life.

BACKGROUND OF THE INVENTION

An attractive method for aseptic packaging of sterile pharmaceutical solutions is an automated process called blow-fill-seal (BFS) technology, wherein plastic containers are formed, filled and sealed in one continuous operation with limited need for human intervention. An advantage of this technology is that the opportunity for microbial contamination is minimized. It has been used for the production of unit dosage vials containing albuterol.

Albuterol is an optically active compound which can exist as an (R)- or an (S)-enantiomer, or as a mixture of the two enantiomers. The term albuterol commonly refers to a racemic mixture of (R)- and (S)-albuterol. Herein, the term albuterol is defined as including a racemic mixture, a single enantiomer of albuterol, or any mixture of enantiomers of albuterol. Albuterol is a β-adrenergic antagonist and acts to relax smooth muscle. It is, therefore, particularly effective as a bronchodilator in the treatment of asthma. Racemic albuterol and racemic albuterol sulfate are commercially available as Proventil®, Ventolin® and Vormax®. The pure (R)-enantiomer, which has the generic name levalbuterol, is commercially available as Xopenex®.

It is known that albuterol degrades in aqueous solution. (See, for example, U.S. Pat. No. 4,499,108, which relates to albuterol sulfate syrups that are stable upon prolonged storage.) The cause(s) and mechanisms of the degradation reaction(s) are not well understood, but it is known that albuterol aldehyde is one of the degradation products. The level of albuterol aldehyde in an albuterol formulation for inhalation is regulated by the Food and Drug Administration because of the potentially negative effects of administering an aldehyde compound to a patient by inhalation. Currently, a maximum of 0.05% by weight albuterol aldehyde is allowed in an albuterol formulation at the time of release, with a maximum of 0.08% at the end of the expiration date. Therefore, formation of albuterol aldehyde in an aqueous albuterol solution limits the shelf life of the package containing it.

One drawback of using BFS technology for formulations of albuterol is that it has been difficult to produce a packaged formulation having a long shelf life without including additives such as chelating agents, sequestering agents, antioxidants or preservatives in the formulation or storing the package at temperatures below room temperature. It is therefore an object of the invention to provide a method of maximizing the shelf life of an albuterol formulation packaged using BFS technology.

SUMMARY OF THE INVENTION

It has been surprisingly found that when nitrogen is used as the blowing or ballooning gas in a BFS process for packaging an albuterol formulation, a package having a long shelf life is obtained. In this respect, the present invention relates to a method for manufacturing a packaged albuterol formulation having a long shelf life comprising:

blowing nitrogen gas through a hollow cylinder of an oxygen-permeable plastic and molding the hollow cylinder into an oxygen-permeable container, thereby at least partially enclosing a reduced oxygen atmosphere;

filling the oxygen-permeable container with an aqueous formulation of albuterol, or a pharmaceutically acceptable salt thereof, the aqueous formulation containing less than 0.05% by weight of albuterol aldehyde and less than 1 ppm dissolved oxygen;

enclosing the oxygen-permeable container in a reduced oxygen atmosphere within an oxygen-impermeable wrapper to produce a package enclosing an atmosphere containing less than about 2% oxygen; whereby the amount of albuterol aldehyde contained in the aqueous formulation remains lower than 0.08% by weight for a period of at least 12 months at room temperature.

In another aspect, the present invention relates to stable packaged pharmaceutical formulations consisting essentially of:

albuterol or a pharmaceutically acceptable salt thereof;

sodium chloride; and water;

the formulation having a pH of about 4, containing less than 0.08% by weight of albuterol aldehyde and less than 1 ppm dissolved oxygen, enclosed within an oxygen-permeable plastic container, and remaining at less than 0.08% by weight of albuterol aldehyde after storage at 40° C. for six months. Preferably, the oxygen-permeable plastic container additionally encloses a gas phase comprising less than about 5% oxygen. The oxygen-permeable plastic container is preferably enclosed within a sealed wrapper comprising an oxygen-impermeable material. More preferably, the sealed wrapper additionally encloses a gas phase contained within the sealed wrapper and comprising less than about 5% oxygen.

DETAILED DESCRIPTION OF THE INVENTION

Figure 1:
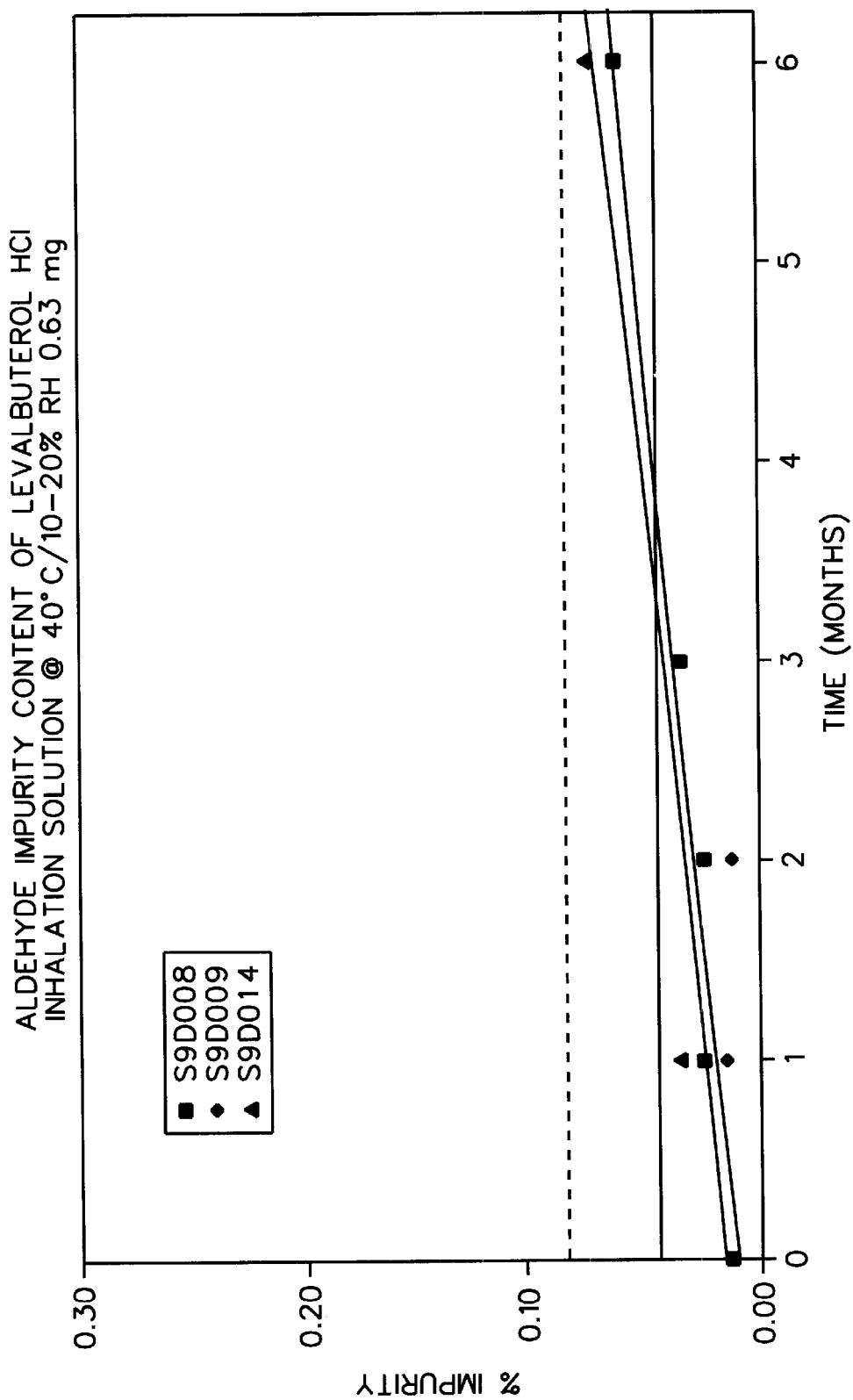
FIG. 1 is a plot of % albuterol aldehyde vs. time for an albuterol formulation packaged using nitrogen as the ballooning gas.

According to the method of the present invention, an aqueous solution of albuterol that has a low level of dissolved oxygen is prepared for packaging. No chelating agent, sequestering agent, antioxidant, or preservative, such as edetate disodium, sodium citrate, or benzalkonium chloride, is included in the formulation. The albuterol utilized in the solution may be racemic albuterol, a single enantiomer of albuterol, or a mixture of enantiomers of albuterol. It may be in the form of the free amine or a pharmaceutically acceptable salt thereof. In a preferred embodiment, (R)-albuterol is used. (R)-Albuterol is defined as containing at least 95% by weight (R)-albuterol, preferably greater than 98% (R)-albuterol, and more preferably greater than 99% (R)-albuterol.

In another preferred embodiment, the (R)-albuterol is in the form of a pharmaceutically acceptable salt. Pharmaceutically acceptable salts of albuterol include, for example, acid addition salts such acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, and p-toluenesulfonic. The hydrochloride salt is especially preferred for (R)-albuterol; the sulfate is preferred for racemic albuterol.

An exemplary formulation, suitable for administration to an adult by inhalation is:

1.4 mg (R)-albuterol hydrochloride 27 mg sodium chloride 3 mL water

A lower dosage may be provided by reducing the amount of (R)-albuterol hydrochloride to 0.7 mg, while keeping the amounts of sodium chloride and water the same. Typical pediatric formulations contain 0.18 mg to 0.36 mg (R)-albuterol hydrochloride per 3 mL unit dose. Oxygen is displaced from the bulk solution by sparging with nitrogen until an oxygen level of less than 1 ppm, preferably, 500 ppb, and more preferably, 300 ppb, is attained. A nitrogen blanket is maintained over the bulk solution until the solution is packaged.

A package for the formulation is made up of an oxygen-permeable container and an oxygen-impermeable wrapper that encloses one or more of the containers. For example, a preferred container is a unit dose vial composed of low density polyethylene (LDPE). In a preferred embodiment, a plurality of unit dose vials are enclosed within an oxygen-impermeable wrapper composed of a foil laminate.

The containers are typically fabricated, filled and sealed using BFS technology. (For an overview of BFS technology, see Oschman, R. and Schubert, O. E., *Blow-Fill-Seal Technology,* CRC Press, 1999.) A plurality of unit dose vials (UDV) is typically formed, filled and sealed simultaneously. An extrudable, oxygen-permeable plastic or resin, preferably LDPE, is used to form the containers. First, the resin is extruded into an opened blow mold in the form of parallel hollow cylinders. The mold plates are closed and simultaneously seal the bottom. A blowing or ballooning gas is passed through the cylinders to maintain the opening in the cylinders while a vacuum is applied through tiny holes in the walls of the mold to fill the mold and form the containers. In prior art processes, compressed air has been used to form the containers, in contrast to the method of the present invention. Nitrogen is used as the ballooning gas in order to reduce the oxygen level in the headspace of the containers being formed. The albuterol solution is measured into the containers and sealed. Typically, the oxygen level is reduced to about 14% in the headspace or gas phase enclosed within the containers.

The vials are then enclosed in a protective oxygen-impermeable wrapper. A material that is impermeable to oxygen and that can be sealed to exclude oxygen may be used. Barrier materials that can prevent the transmission of oxygen are well known in the art and include commercially available polymer films and metallic foils such as aluminum foil. Laminates composed of one or more barrier materials and one or more films of a non-barrier polymer may also be used. A suitable material, for example, is a laminated foil composed of layers of polyester, aluminum foil and polyethylene. As the pouch is sealed, nitrogen is blown into the interior of the pouch, reducing the level of oxygen in the interior of the sealed pouch to less than about 2%.

After the pouch is sealed, oxygen diffuses from the headspace of the vials into the interior of the pouch until an equilibrium is reached at less than about 5% oxygen in the headspace of both the vials and the pouch. The diffusion occurs over a period of time and may take as long as two weeks.

It has been unexpectedly found that packages manufactured without using nitrogen as the ballooning gas have higher levels of albuterol aldehyde over time than those produced using nitrogen. In addition, when nitrogen was used as the ballooning gas, but wrapping of the vials was delayed, higher levels of albuterol aldehyde can result.

EXAMPLES

Example 1

A solution of (R)-albuterol was prepared according to the formula:

1.44 mg (R)-albuterol hydrochloride 27 mg sodium chloride 3 mL water.

The pH of the solution was adjusted with sulfuric acid. The solution was sparged with nitrogen until the level of oxygen was less than 500 ppb. The tank was blanketed with nitrogen.

The solution was packaged in unit dose vials using a BFS method. A set of twelve vials were formed simultaneously from LDPE using nitrogen as the ballooning gas and then filled with the solution. A pouch composed of a laminate of aluminum foil, polyester and polyethylene was formed around the set of filled UDVs. A wand for the delivery of nitrogen was placed inside the assembly, and nitrogen was blown into the pouch as it was being formed and sealed. The level of oxygen in the airspace in the pouch was reduced to less than 2%. Pouches thus manufactured were held at 40° C. and samples were withdrawn at intervals of 1, 2, 3, and 6 months and tested for levels of albuterol aldehyde. Results are displayed graphically in FIG. 1. The graph shows that the level of albuterol aldehyde was below the FDA release limit of 0.05% initially and remained below 0.08% for at least six months. This corresponds to a shelf life of at least 12 months at room temperature.

Example 2

A solution of (R)-albuterol was prepared as in Example 1. The solution of (R)-albuterol was then packaged in unit dose vials as in Example 1, except that nitrogen was not used as the ballooning gas. The UDVs were wrapped in a laminated foil pouch with nitrogen, also as in Example 1.

Figure 2:
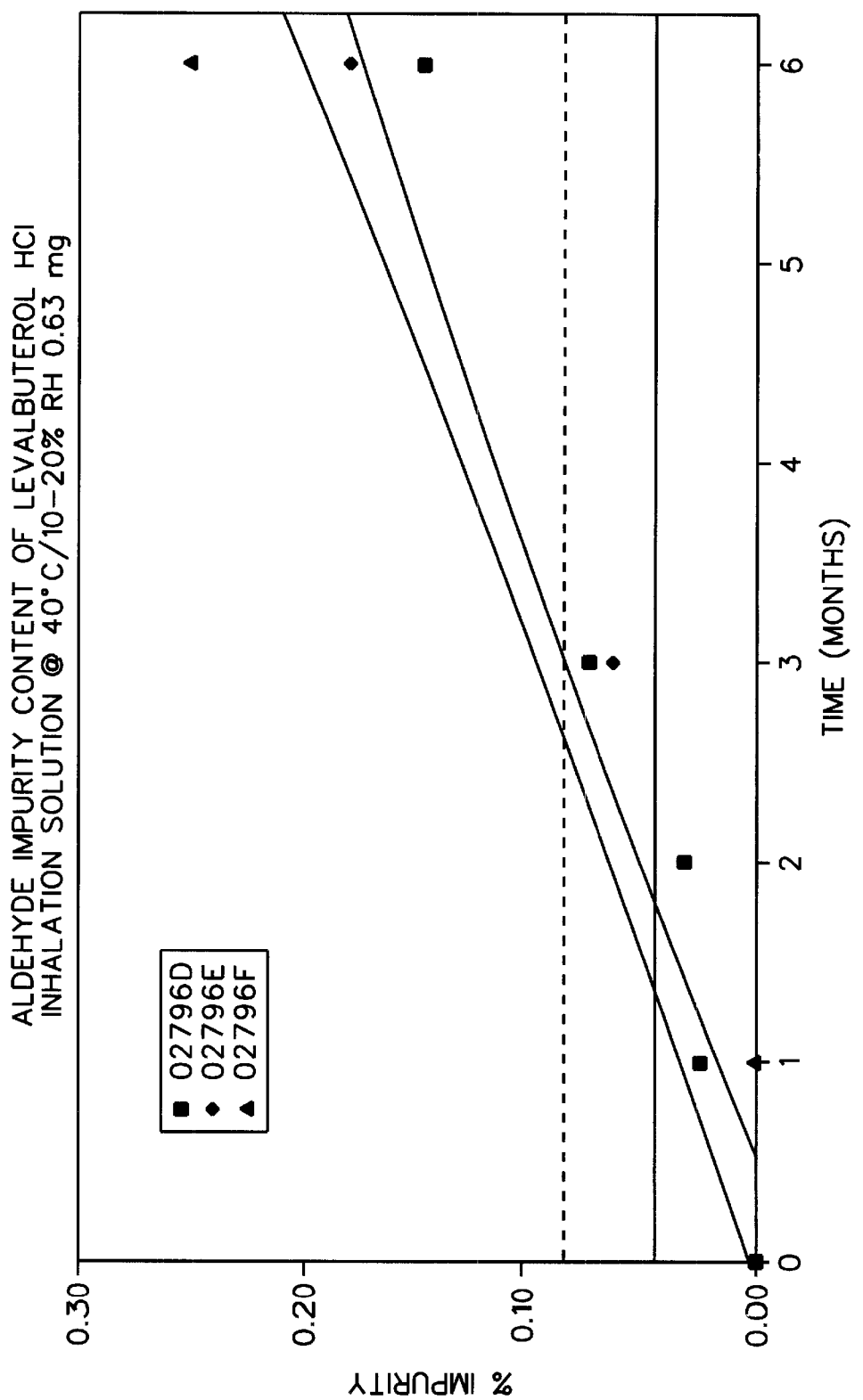
FIG. 2 is a plot of % albuterol aldehyde vs. time for an albuterol formulation packaged without using nitrogen.

Pouches were held at 40° C. and samples were withdrawn at intervals of 1, 2, 3, and 6 months and tested for levels of albuterol aldehyde. Results are displayed graphically in FIG. 2. The graph shows that the level of albuterol aldehyde rose above 0.08% in less than three months. This corresponds to a shelf life of significantly less than 12 months at room temperature.

Example 3

Figure 3:
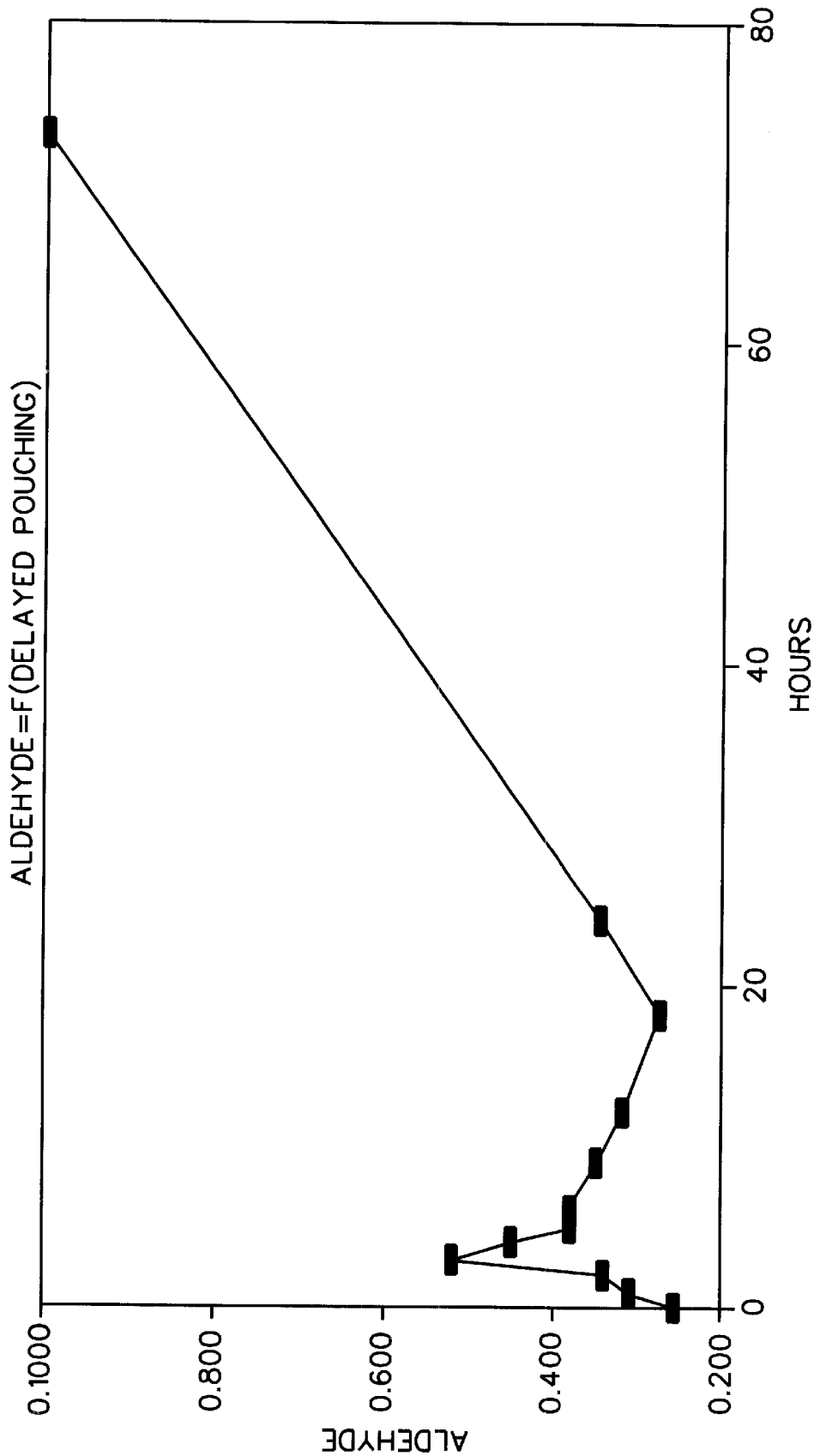
FIG. 3 is a plot of % albuterol aldehyde vs. delay time for an albuterol formulation wherein containers were filled with the formulation and wrapping of the containers was delayed. % Albuterol aldehyde was determined after storage at 40° C. for three months.

A solution of (R)-albuterol was prepared and packaged as in Example 1, except that pouching of the UDVs was delayed. Levels of albuterol aldehyde in the solution were measured for various delay times. Results are tabulated below and displayed graphically in FIG. 3. The results indicate that delayed pouching can increase the level of albuterol aldehyde in the solution.

TABLE 1

Delayed Pouching of UDVs: % Albuterol Aldehyde After 3 Months 40 C/15% RH

| Sample Type: | Replicate #: | Albuterol Aldehyde Values |
|---|---|---|
| Positive Control | 1 | 0.03 |
| | 2 | 0.02 |
| | 3 | NA |
| Negative Control | 1 | 0.10 |
| | 2 | 0.09 |
| | 3 | 0.11 |
| 1 Hour | 1 | 0.03 |
| | 2 | 0.03 |
| | 3 | 0.03 |
| 2 Hour | 1 | 0.03 |
| | 2 | 0.04 |
| | 3 | 0.03 |
| 3 Hour | 1 | 0.06 |
| | 2 | 0.03 |
| | 3 | 0.06 |
| 4 Hour | 1 | 0.05 |
| | 2 | 0.05 |
| | 3 | 0.03 |
| 5 Hour | 1 | 0.05 |
| | 2 | 0.03 |
| | 3 | 0.03 |
| 6 Hour | 1 | 0.04 |
| | 2 | 0.04 |
| | 3 | 0.03 |
| 9 Hour | 1 | 0.04 |
| | 2 | 0.03 |
| | 3 | 0.03 |
| 12 Hour | 1 | 0.03 |
| | 2 | 0.03 |
| | 3 | 0.03 |
| 18 Hour | 1 | 0.02 |
| | 2 | 0.03 |
| | 3 | 0.03 |
| 24 Hour | 1 | 0.03 |
| | 2 | 0.03 |
| | 3 | 0.04 |

What is claimed is:

1. A method of manufacturing a packaged albuterol formulation having a shelf life of at least twelve months; said method comprising:

blowing nitrogen gas through a hollow cylinder of an oxygen-permeable plastic and molding the hollow cylinder into an oxygen-permeable container, thereby at least partially enclosing a reduced oxygen atmosphere;

filling the oxygen-permeable container with an aqueous formulation of albuterol, or a pharmaceutically acceptable salt thereof, said aqueous formulation being free of chelating agents, sequestering agents, antioxidants, and preservatives, and containing less than 0.05% by weight of albuterol aldehyde and less than 1 ppm dissolved oxygen;

enclosing the oxygen-permeable container under an atmosphere containing less than about 2% by weight oxygen within an oxygen-impermeable wrapper to produce a package enclosing an atmosphere containing less than about 2% by weight oxygen, and which does not contain an oxygen-absorbent.

2. A stable packaged preservative-free pharmaceutical formulation consisting essentially of:

albuterol or a pharmaceutically acceptable salt thereof;
sodium chloride; and
water;

said formulation having a pH of about 4, containing less than 0.08% by weight of albuterol aldehyde and less than 1 ppm dissolved oxygen, enclosed within an oxygen-permeable plastic container, and remaining at less than 0.08% by weight of albuterol aldehyde after storage at 40° C. for six months;

wherein said formulation does not contain a chelating agent, a sequestering agent, an antioxidant, or a preservative.

3. A stable packaged pharmaceutical formulation according to claim 2 wherein said oxygen-permeable plastic container additionally encloses a gases phase comprising less than about 5% oxygen.

4. A stable packaged pharmaceutical formulation according to claim 2 wherein said oxygen-permeable plastic container is enclosed within a sealed wrapper comprising an oxygen-impermeable material.

5. A stable packaged pharmaceutical formulation according to claim 4 wherein said sealed wrapper additionally encloses a gas phase contained within the sealed wrapper and comprising less than about 5% by weight oxygen.

6. A stable packaged pharmaceutical formulation according to claim 4 wherein a plurality of oxygen-permeable plastic containers are enclosed within said sealed wrapper.

7. A stable packaged pharmaceutical formulation according to claim 2 wherein said albuterol is (R)-albuterol.

8. A stable packaged pharmaceutical formulation according to claim 7 wherein said pharmaceutically acceptable salt is (R)-albuterol hydrochloride.

9. A stable packaged pharmaceutical formulation according to claim 2 wherein said oxygen-impermeable material is a foil laminate.

10. A stable packaged pharmaceutical formulation according to claim 2 wherein said oxygen-permeable material is low density polyethylene.

11. A preservative-free unit dosage formulation for administration by inhalation consisting essentially of:

0.18–1.4 mg albuterol or a pharmaceutically acceptable salt thereof;
27 mg sodium chloride; and
2–4 mL water;

said unit dosage formulation having a pH of about 4, containing less than 1 ppm dissolved oxygen and containing less than 0.08% by weight of albuterol aldehyde after storage at 40° C. for six months;

wherein said unit dosage formulation does not contain a chelating agent, a sequestering agent, an antioxidant, or a preservative.

12. A stable, preservative-free packaged pharmaceutical formulation, packaged according to the method of claim 1, said formulation comprising:

albuterol or a pharmaceutically acceptable salt thereof;
sodium chloride; and
having a pH of about 4, containing less than 0.08% by weight of albuterol aldehyde and less than 1 ppm dissolved oxygen, and remaining at less than 0.08% by weight of albuterol aldehyde after storage at 40° C. for six months;

wherein said formulation does not contain a ch elating agent, a sequestering agent, an antioxidant, or a preservative. agent, an antioxidant, or a preservative.

13. A stable, preservative-free packaged pharmaceutical formulation according to claim 12, wherein said albuterol is (R)-albuterol.

14. A stable, preservative-free packaged pharmaceutical formulation according to claim 12 wherein said pharmaceutically acceptable salts is (R)-albuterol hydrochloride.

15. A stable, preservative-free packaged pharmaceutical formulation according to claim 12 wherein said oxygen-impermeable material is a foil laminate.

16. A stable, preservative-free packaged pharmaceutical formulation according to claim 12 wherein said oxygen-permeable material is low density polyethylene.

17. A method according to claim 1 wherein said albutrol is (R)-albuterol.

18. A method according to claim 1 wherein said pharmaceutically acceptable salt is (R)-albuterol hydrochloride.

19. A method according to claim 1 wherein said oxygen-impermeable wrapper comprises a foil laminate.

20. A method according to claim 1 wherein said oxygen-permeable container comprises low density polethylene.

* * * * *

UNITED STATES PATENT AND TRADEMARK OFFICE
CERTIFICATE OF CORRECTION

PATENT NO. : 6,451,289 B2
DATED : September 17, 2002
INVENTOR(S) : Wherry, III et al.

It is certified that error appears in the above-identified patent and that said Letters Patent is hereby corrected as shown below:

Column 6,
Line 1, delete the word "permeable"
Line 58, delete "agent, an antioxident, or a preservative."

Signed and Sealed this

Twelfth Day of August, 2003

JAMES E. ROGAN
*Director of the United States Patent and Trademark Office*